United States Patent
Kaneko et al.

(10) Patent No.: US 9,795,520 B2
(45) Date of Patent: Oct. 24, 2017

(54) DISPOSABLE DIAPER

(71) Applicant: UNICHARM CORPORATION, Shikokuchuo-shi, Ehime (JP)

(72) Inventors: Tomohiro Kaneko, Kanonji (JP); Toshimitsu Baba, Kanonji (JP); Kaori Minami, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 393 days.

(21) Appl. No.: 14/430,374

(22) PCT Filed: Sep. 4, 2013

(86) PCT No.: PCT/JP2013/073831
§ 371 (c)(1),
(2) Date: Mar. 23, 2015

(87) PCT Pub. No.: WO2014/050473
PCT Pub. Date: Apr. 3, 2014

(65) Prior Publication Data
US 2015/0230995 A1    Aug. 20, 2015

(30) Foreign Application Priority Data
Sep. 28, 2012  (JP) ................. 2012-218618

(51) Int. Cl.
*A61F 13/49* (2006.01)
*A61F 13/496* (2006.01)

(52) U.S. Cl.
CPC ...... *A61F 13/49011* (2013.01); *A61F 13/496* (2013.01); *A61F 2013/49025* (2013.01); *A61F 2013/49038* (2013.01)

(58) Field of Classification Search
CPC .......... A61F 13/49011; A61F 13/49012; A61F 13/49014; A61F 13/49015; A61F 13/496;
(Continued)

(56) References Cited

U.S. PATENT DOCUMENTS 6,902,793 B2 * 6/2005 Ukegawa .......... A61F 13/49011
428/181
2003/0031834 A1   2/2003 Ukegawa et al.
(Continued)

FOREIGN PATENT DOCUMENTS

CN    101484308 A    7/2009
EP      2039504 A1    3/2009
(Continued)

OTHER PUBLICATIONS

International Search Report mailed Nov. 26, 2013 in International Application No. PCT/JP2013/073831 filed Sep. 4, 2013.

*Primary Examiner* — Lynne Anderson
(74) *Attorney, Agent, or Firm* — Hauptman & Ham, LLP

(57) ABSTRACT

A disposable diaper includes a waist opening and a pair of leg openings with a composite stretchable member. The composite stretchable member includes first and second nonwoven fabric sheet parts and elastic members arranged therebetween. Each of the first and second nonwoven fabric sheet parts is provided with a plurality of convex-concave regions including convex and concave parts. At least one non-shaped region separates the convex-concave regions from each other in the longitudinal direction. The first and second nonwoven fabric sheet parts are overlaid so that the convex-concave regions of the first nonwoven fabric sheet part and the second nonwoven fabric sheet part adjoin each other and the non-shaped regions of the first nonwoven fabric sheet part and the second nonwoven fabric sheet part are separated from each other and are joined with each other by an adhesive applied to the elastic members.

7 Claims, 20 Drawing Sheets

(58) Field of Classification Search
CPC .. A61F 2013/49023; A61F 2013/49025; A61F 2013/49038
See application file for complete search history.

(56) References Cited

U.S. PATENT DOCUMENTS

2006/0270302 A1 11/2006 Ando et al.
2009/0275909 A1 11/2009 Sakaguchi
2014/0302286 A1 10/2014 Okuda et al.

FOREIGN PATENT DOCUMENTS

| EP | 2767267 A1 | 8/2014 |
|----|------------|--------|
| JP | 2005-080859 A | 3/2005 |
| JP | 2012-095936 A | 5/2012 |
| JP | 2012-126140 A | 7/2012 |
| JP | 2013-081715 A | 5/2013 |

* cited by examiner

FIG. 10
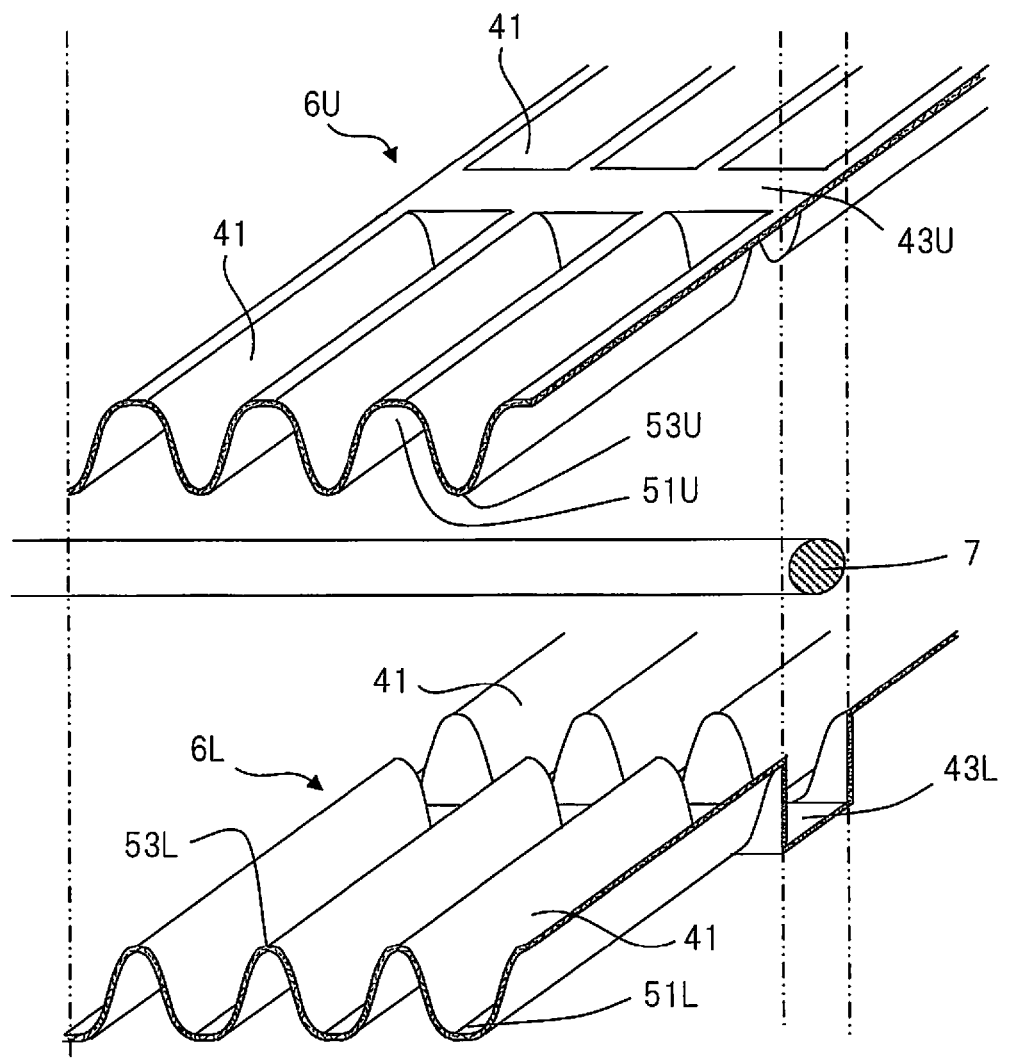
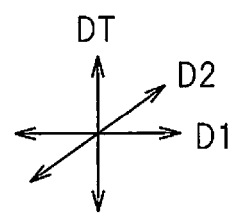

DISPOSABLE DIAPER

RELATED APPLICATIONS

The present application is a National Phase of International Application Number PCT/JP2013/073831, filed Sep. 4, 2013, which claims priority to Japanese Application Number 2012-218618, filed Sep. 28, 2012.

TECHNICAL FIELD

The present invention relates to a disposable diaper.

BACKGROUND ART

Known in the art is a composite stretchable member which has two sheets and a stretch part which is comprised of a plurality of elastic members which are arranged between these two sheets, in which composite stretchable member the two sheets are intermittently joined together in a stretch direction of the stretch part and a direction perpendicular to the stretch direction, the elastic members are arranged at the stretch part so as not to pass through the joined parts of the two sheets and are fastened to the two sheets at their two end parts, and each of the two sheets forms a plurality of pleats which extend continuously along the plurality of elastic members (see PTL 1).

Furthermore, PTL 1 shows such a composite stretchable member arranged at a waist opening part or waist side parts of a disposable diaper. Such a composite stretchable member can form a gather part (stretch part which has large number of pleats) with a soft feel at an absorbent product etc.

CITATIONS LIST

Patent Literature

PTL 1: Japanese Patent Publication No. 2005-80859A

SUMMARY OF INVENTION

Technical Problem

When putting a pants type of disposable diaper on a wearer, the legs of the wearer contact the waist part, in particular the side parts of the waist part, whereby force acts on these parts in a direction of passage of the legs of the wearer. At this time, in a disposable diaper where a composite stretchable member as shown in PTL 1 is arranged at the above parts, the composite stretchable member may receive force in a direction of passage of the legs of the wearer whereby contraction of the mutually joined sheets causes deformation in the thickness direction and large pleats. At this time, the legs of the wearer are liable to end up being caught in such pleats and putting on the disposable diaper is liable to become difficult.

Therefore, an object of the present invention is to provide a disposable diaper which is easily put on a wearer.

Solution to Problem

To achieve the above object, the present invention provides a disposable diaper which is provided with a waist opening and a pair of leg openings, wherein the disposable diaper includes a longitudinal direction and a transverse direction which is perpendicular to the longitudinal direction, a composite stretchable member is provided at least at side parts of a waist part which is positioned between the waist opening and the leg openings of the disposable diaper, the composite stretchable member is provided with a first nonwoven fabric sheet part and a second nonwoven fabric sheet part which are mutually overlaid as well as elastic members which are arranged between the first nonwoven fabric sheet part and the second nonwoven fabric sheet part, each of the first nonwoven fabric sheet part and the second nonwoven fabric sheet part is provided with a plurality of convex-concave regions which are provided with convex parts and concave parts which are alternately repeated along the transverse direction and which extend in the longitudinal direction and at least one non-shaped region which separates these convex-concave regions from each other in the longitudinal direction, the first nonwoven fabric sheet part and the second nonwoven fabric sheet part are overlaid so that the convex-concave regions of the first nonwoven fabric sheet part and the second nonwoven fabric sheet part adjoin each other and the non-shaped regions of the first nonwoven fabric sheet part and the second nonwoven fabric sheet part are separated from each other and so that the convex-concave regions and the non-shaped regions are respectively aligned in the longitudinal direction, and the first nonwoven fabric sheet part and the second nonwoven fabric sheet part are joined with each other by an adhesive which is applied to the elastic members.

Advantageous Effects of Invention

According to the present invention, it is possible to provide a disposable diaper which is easily put on a wearer.

Below, the present invention will be understood more sufficiently from the attached drawings and preferred embodiments of the present invention.

BRIEF DESCRIPTION OF DRAWINGS

FIG. 10 is an exploded view of a composite stretchable member in FIG. 9.

DESCRIPTION OF EMBODIMENTS

The present invention will be described in detail while referring to the above drawings. Note that, the figures are sometimes not drawn to the same sizes, scales, and shapes of component elements as the actual ones in order to facilitate understanding of the present invention and simplify the drawings.

The disposable diaper of the present invention is a so-called pants type diaper and, for example, includes 3P (three-piece), side panel, all-in-one, inner-outer, and any structures and shapes of disposable diapers.

First Embodiment

Figure 1:
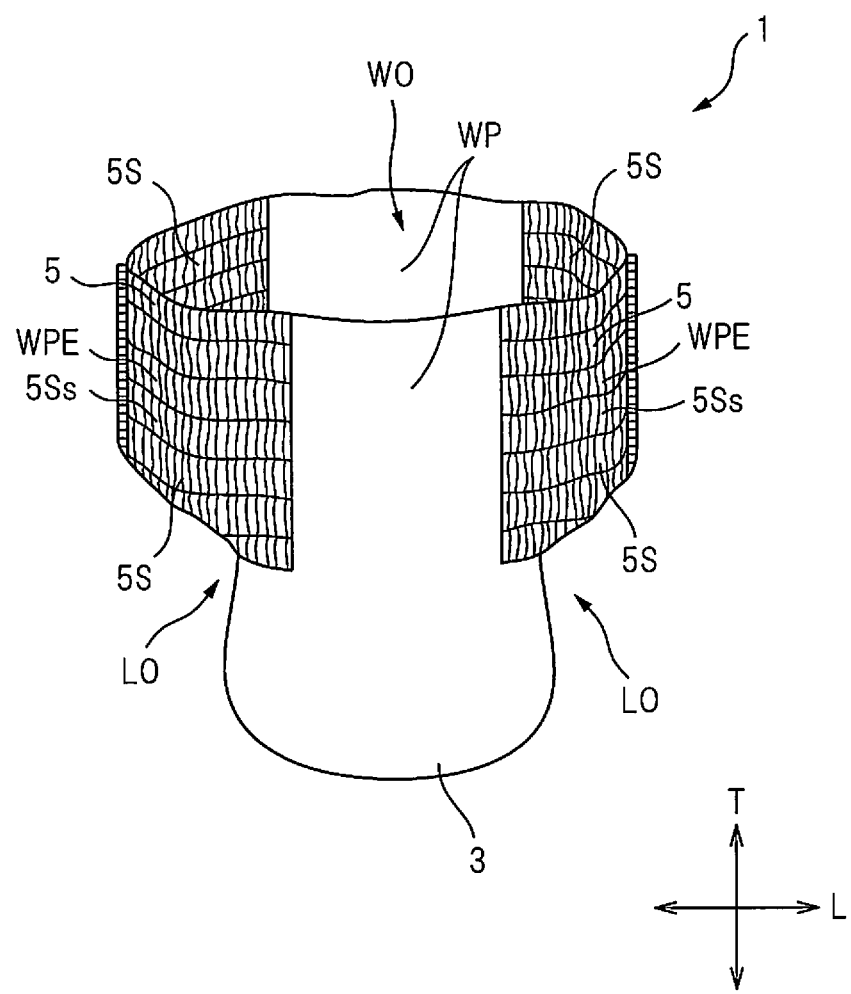
FIG. 1 is a front bird's eye view which shows a disposable diaper of a first embodiment.
Figure 2:
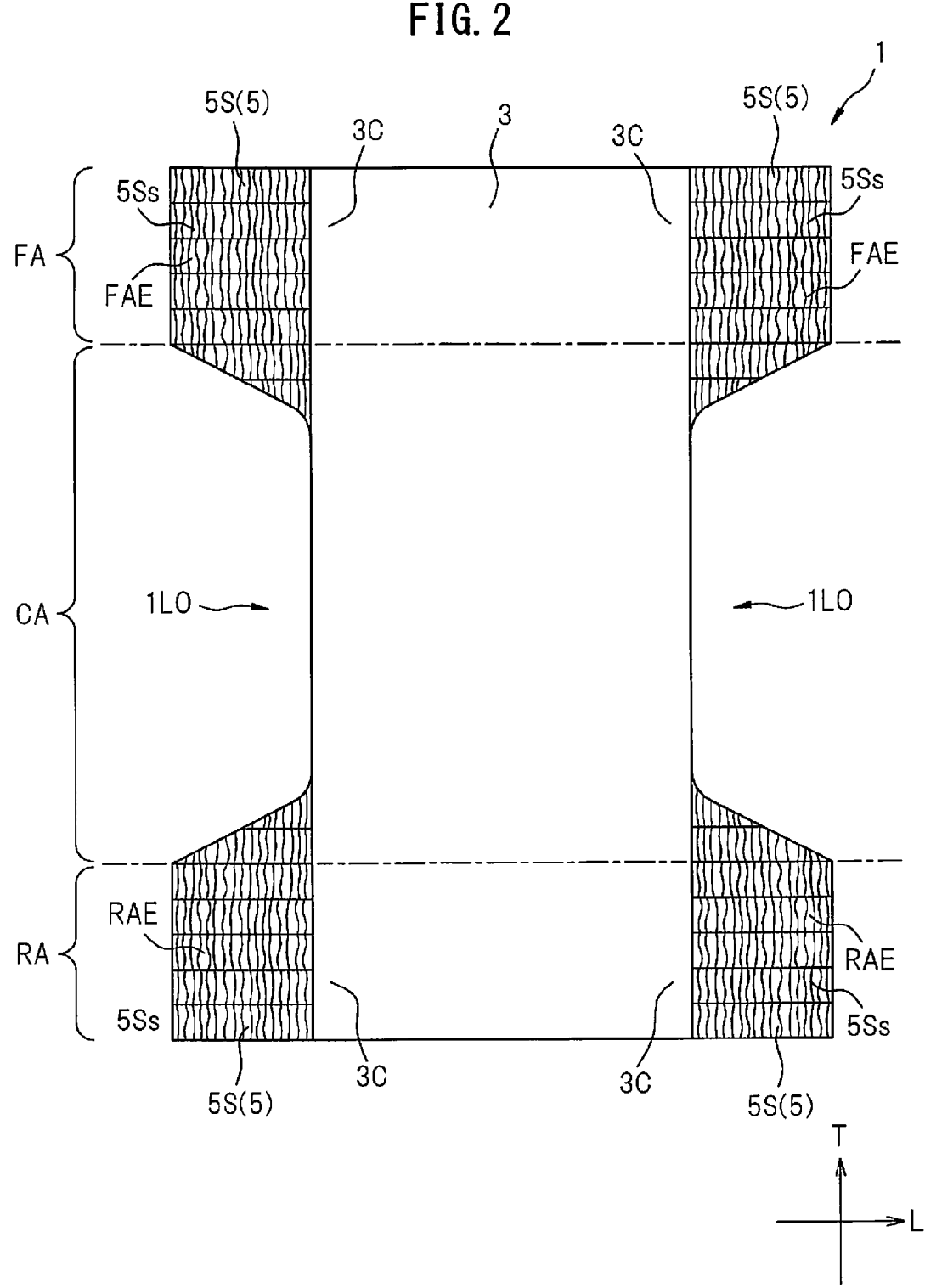
FIG. 2 is a laid open view of the disposable diaper in FIG. 1.

FIG. 1 is a front bird's eye view which shows a disposable diaper 1 of a first embodiment which is provided with a single waist opening WO and a pair of leg openings LO. The disposable diaper 1 of the first embodiment is a so-called side panel type of disposable diaper. FIG. 2 is a laid open view of a disposable diaper 1 in FIG. 1. In FIG. 2, a front area FA and a rear area RA are separated in the longitudinal direction T. Between the front area FA and the rear area RA, a crotch area CA is positioned. Note that, regarding the description of the pleats which form at the later explained convex-concave regions 41 in the drawing, sometimes not everything is described from the viewpoint of ease of viewing of the drawing.

The disposable diaper 1 of the first embodiment includes at least an absorbent element 3 which is comprised of a top sheet, a back sheet, and an absorber which is arranged between the top sheet and back sheet and includes four side panels 5S which are formed from the composite stretchable member 5 and are joined to the absorbent element 3. Referring to FIG. 2, the absorbent element 3 extends from the front area FA through the crotch area CA to the rear area RA, that is, from the stomach side of the wearer past through his/her crotch to the back side in the longitudinal direction T.

The top sheet is provided at a skin contact side which contacts the skin of the wearer when the diaper is put on. The top sheet is formed by a liquid-permeable sheet such as hydrophilic nonwoven fabric, woven fabric, permeable plastic film and permeable hydrophobic nonwoven fabric.

The back sheet is provided at a reverse side of the top sheet. The back sheet is formed from a leak preventing (liquid impermeable) plastic film, a liquid permeation resistant fiber nonwoven fabric, laminate of them, etc. For example, it can be mainly formed from a plastic film, laminate of a nonwoven fabric and plastic film, etc.

The absorber absorbs bodily fluids of the wearer and is formed by an absorbent core made of a pulverized pulp, highly absorbent polymer, etc., and an absorbent sheet such as tissue which covers the absorbent core.

In the first embodiment, the side panels 5S are joined with the side parts 3C at the two end parts of the absorbent element 3 in the longitudinal direction when the diaper is laid open. The side panels 5S which are arranged at the sides of the absorbent element 3 in the transverse direction (right side and left side of FIG. 2) are joined with each other at these side edge parts 5Ss. The side panels 5S form substantially rectangular shapes at the front area FA and rear area RA. At the crotch area CA, the width of the side panels 5S becomes narrower the further toward the center of the disposable diaper 1 in the longitudinal direction T. In this disposable diaper 1, due to the part positioned at the crotch area CA which has a width narrower than the part positioned at the front area FA and rear area RA, leg opening forming parts 1LO which form the leg openings LO are formed.

In the disposable diaper 1 of the first embodiment, the waist part WP is formed by the absorbent element 3 and the side panels 5S which are positioned at the front area FA and rear area RA. Further, at the side parts WPE of the waist part including the side edge parts FAE and RAE of the front area FA and rear area RA, the side panels 5S and in turn the composite stretchable member 5 are provided.

From here, the composite stretchable member 5 will be explained. First, an example of the method of production of a composite stretchable member 5 will be explained.

Figure 3:
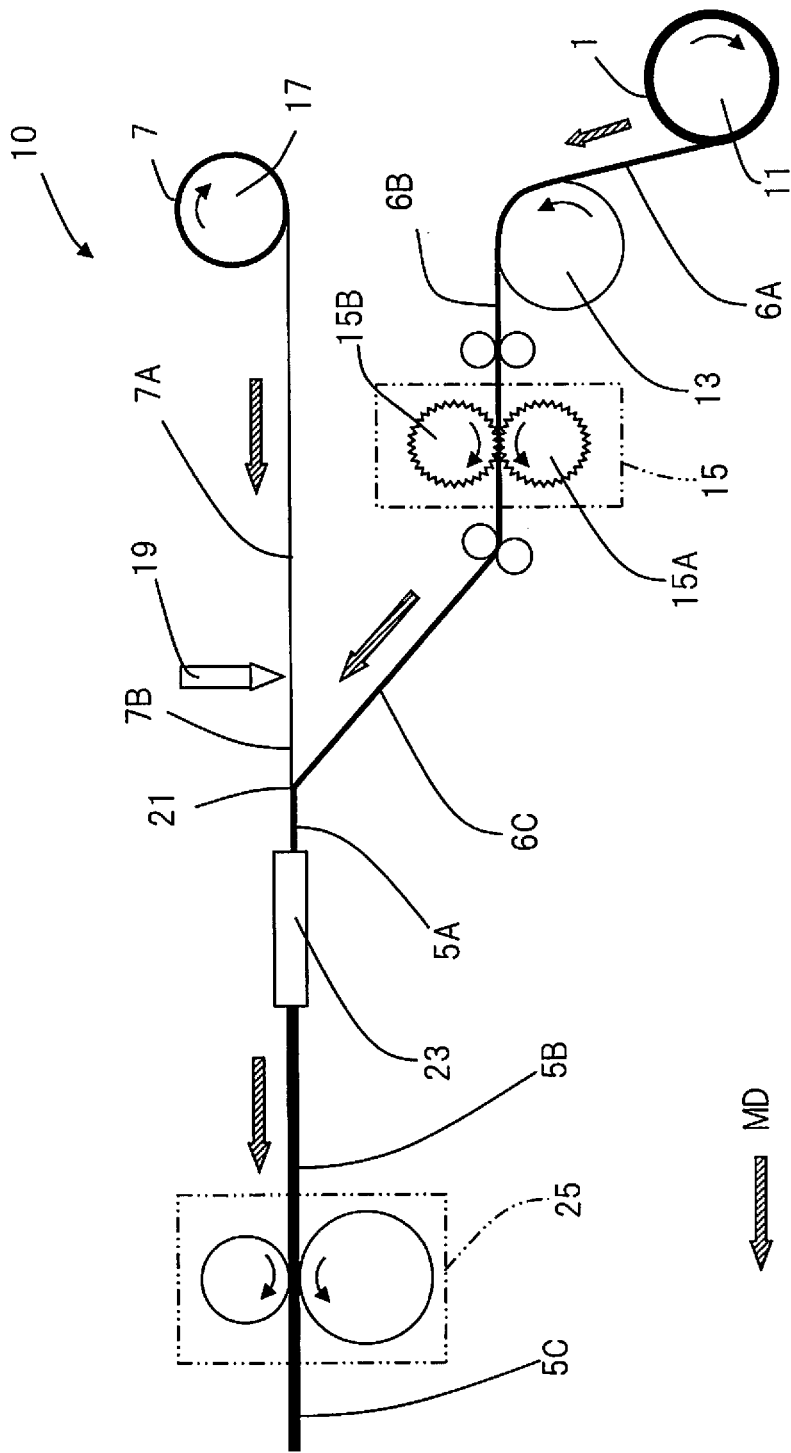
FIG. 3 is a schematic view of an apparatus for producing a composite stretchable member.

FIG. 3 is a schematic view of an apparatus 10 for producing a composite stretchable member 5. Referring to FIG. 3, the nonwoven fabric sheet 6 which forms the composite stretchable member 5 is held wound around the nonwoven fabric sheet feedout part 11. From there, the nonwoven fabric sheet 6 is unrolled in a machine direction MD, that is, a first direction D1 (FIG. 4, etc.) and transferred to a preheating roll 13. The preheating roll 13 preheats the rolled out nonwoven fabric sheet 6A so as to easily deform. In this example, it is set to 50 to 130° C. The preheating temperature is determined in accordance with the type of the nonwoven fabric.

The preheated nonwoven fabric sheet 6B is next transferred to a shaping device 15. The shaping device 15 is comprised of a discontinuous gear roll 15A and continuous gear roll 15B. In this example, like the preheating roll 13, it is set in temperature to 50 to 130° C. to facilitate shaping it in the same way as the preheating roll 13.

Figure 4:
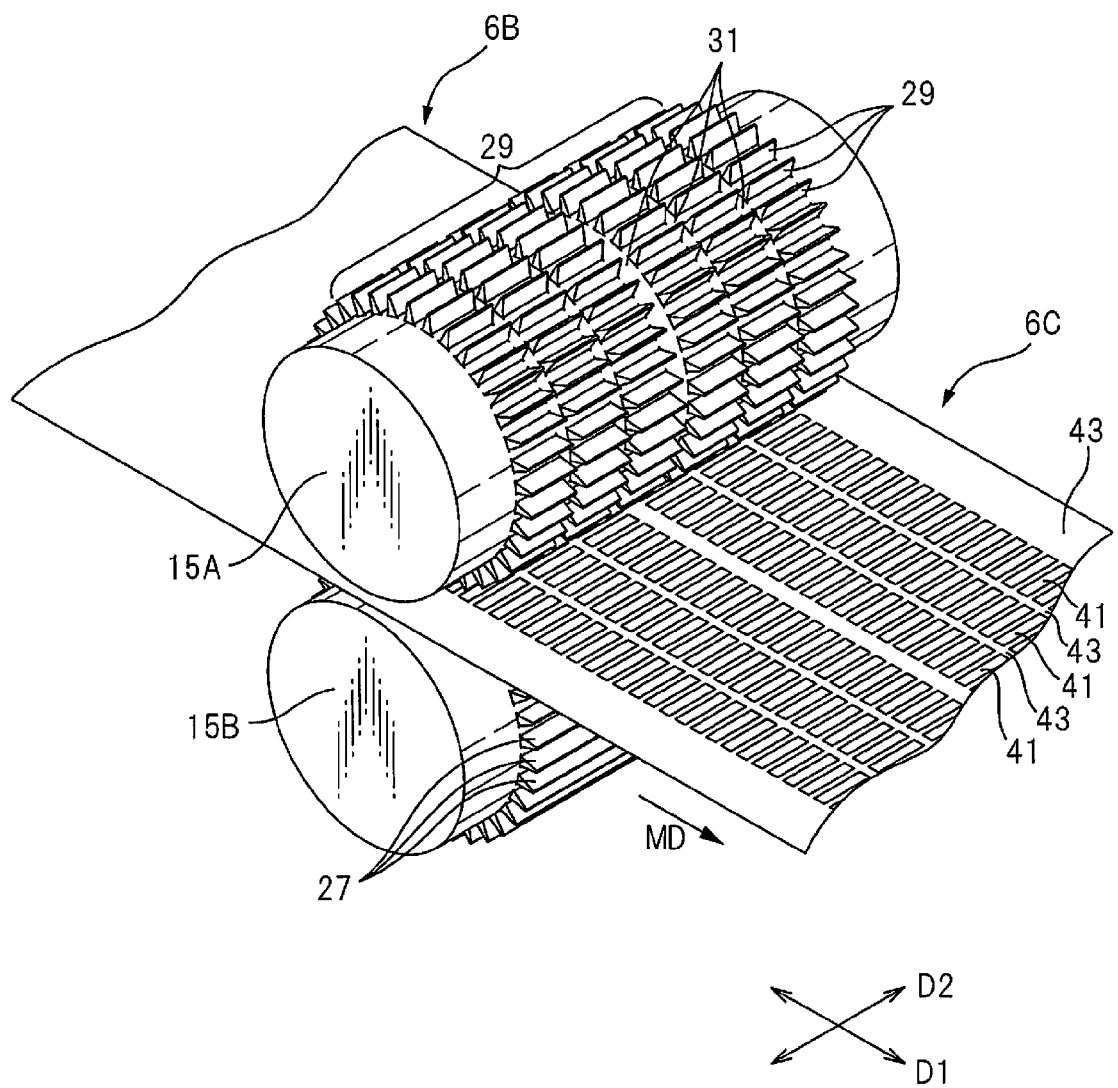
FIG. 4 is a perspective view of a discontinuous gear roll and continuous gear roll of a shaping device of the apparatus for producing a composite stretchable member.

FIG. 4 shows a perspective view of a discontinuous gear roll 15A and continuous gear roll 15B according to this example and a schematic view of a shaped nonwoven fabric sheet 6C. Note that, in FIG. 4 and FIG. 5, the positions of the discontinuous gear roll 15A and continuous gear roll 15B in FIG. 3 are shown reversed. As shown in FIG. 4, the continuous gear roll 15B has a plurality of continuous teeth 27 which are separated from each other in the circumferential direction. Each of these continuous teeth 27 continues in the width direction. Further, the discontinuous gear roll 15A has a plurality of discontinuous teeth 29 which are separated from each other in the circumferential direction. Each of these discontinuous teeth 29 is interrupted in the width direction by at least one discontinuous part 31. These discontinuous parts 31 are aligned in the circumferential direction.

The preheated nonwoven fabric sheet 6B is passed between these discontinuous gear roll 15A and continuous gear roll 15B which intermesh with each other and rotate in opposite directions to each other. This being so, the nonwoven fabric sheet 6B is partially stretched in the first direction D1 and concave parts 51 and convex parts 53 (FIG. 9) are formed extending along a transverse direction of the nonwoven fabric sheet 6 which is perpendicular to the first direction D1 and constitutes a second direction D2. The concave parts 51 and convex parts 53 which are repeatedly, alternately formed in the first direction D1 (FIG. 9) define convex-concave regions 41. These convex-concave regions 41 are formed at the nonwoven fabric sheet 6C separated by non-shaped regions 43.

Figure 5:
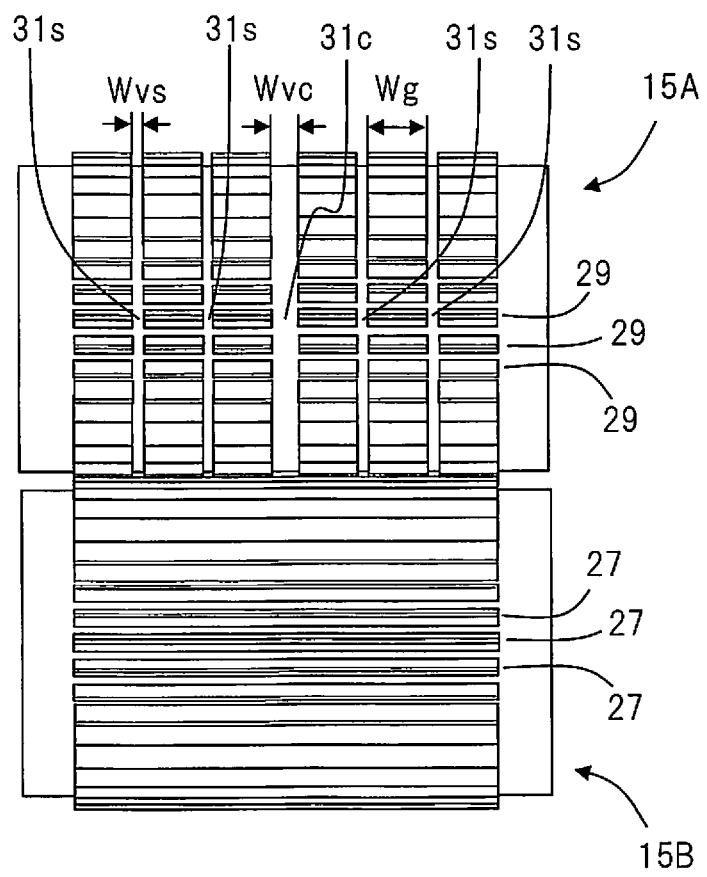
FIG. 5 is a front view of a discontinuous gear roll and continuous gear roll in FIG. 4.

FIG. 5 is a front view of a discontinuous gear roll 15A and continuous gear roll 15B in FIG. 4. In this example, the width Wvc of the discontinuous part 31c at the center of the discontinuous gear roll 15A is 2 mm, while the widths Wvs of the discontinuous parts 31s other than the discontinuous part at the center of the discontinuous gear roll 15A are 1 mm. The widths Wg of the continuous parts of the discontinuous teeth 29 are all the same 4 mm. However, the dimensions of the components of the discontinuous gear roll 15A and the continuous gear roll 15B are not limited to the above dimensions. The center of the center discontinuous part 31c is wider in width than the other discontinuous parts 31s, since it is the part where the nonwoven fabric sheet 6 is folded in the later explained step of folding the nonwoven fabric sheet 6.

Note that, in this example, the discontinuous gears 29 are arranged in six rows in the second direction D2. However, this number of rows of the discontinuous teeth 29 is for simplification of the figure. In actuality, the rows of the discontinuous teeth 29 become greater than this in accordance with the size of the disposable diaper 1 of the first embodiment. The number of rows of the discontinuous teeth 29 can be changed in accordance with the size of the disposable diaper 1, the dimensions of the various portions of the shaping device 15, etc.

Figure 6:
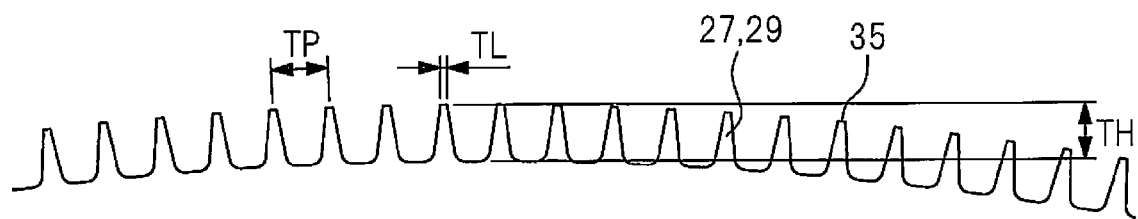
FIG. 6 is a side enlarged view of a discontinuous gear roll or continuous gear roll in FIG. 4.

FIG. 6 shows a partial side view of the discontinuous gear roll 15A and continuous gear roll 15B in FIG. 4. In this example, the discontinuous gear roll 15A and continuous gear roll 15B have heights TH of the teeth 27 and 29 of about 1 mm, while have pitches TP between the top parts of the adjoining teeth 27 and 29 of 1 mm. Further, the teeth 27 and 29 have flat parts 35 at their top parts. The flat parts 35 have lengths TL in the circumferential direction of about 0.1 mm. However, the dimensions of the components of the discontinuous gear roll 15A and the continuous gear roll 15B are not limited to the above dimensions.

Returning to FIG. 3, yarn-like elastic members 7 are stored wound around an elastic member feed out part 17. From there, the elastic members 7 are unrolled and thereby transferred to an adhesive applying part 19. The elastic members 7 are given a certain tension in advance. The later steps are performed with that tension held as it is. In this example, tension is given to the elastic members 7 so that the elastic member stretch-bond ratio (=(length of elastic material in stretched state when bonded with nonwoven fabric sheet part)/(length of elastic material in contracted state)) becomes 3.

The adhesive applying part 19 applies an adhesive on the elastic members 7A which are transported from the elastic member feed out part 17.

Note that, in this example, the adhesive applying part 19 performs slit type continuous coating where it runs the elastic members 7A along a part discharging the adhesive from a slit nozzle (not shown) so as to apply the adhesive around the elastic members 7A. Here, the adhesive is a hot melt adhesive, but the invention is not limited to this.

Next, at a merging part 21, the elastic members 7B on which the adhesive was coated are placed on the non-shaped regions 43 of the shaped nonwoven fabric sheet 6C. The composite stretchable member 5A at this time is shown in FIG. 7.

Figure 7:
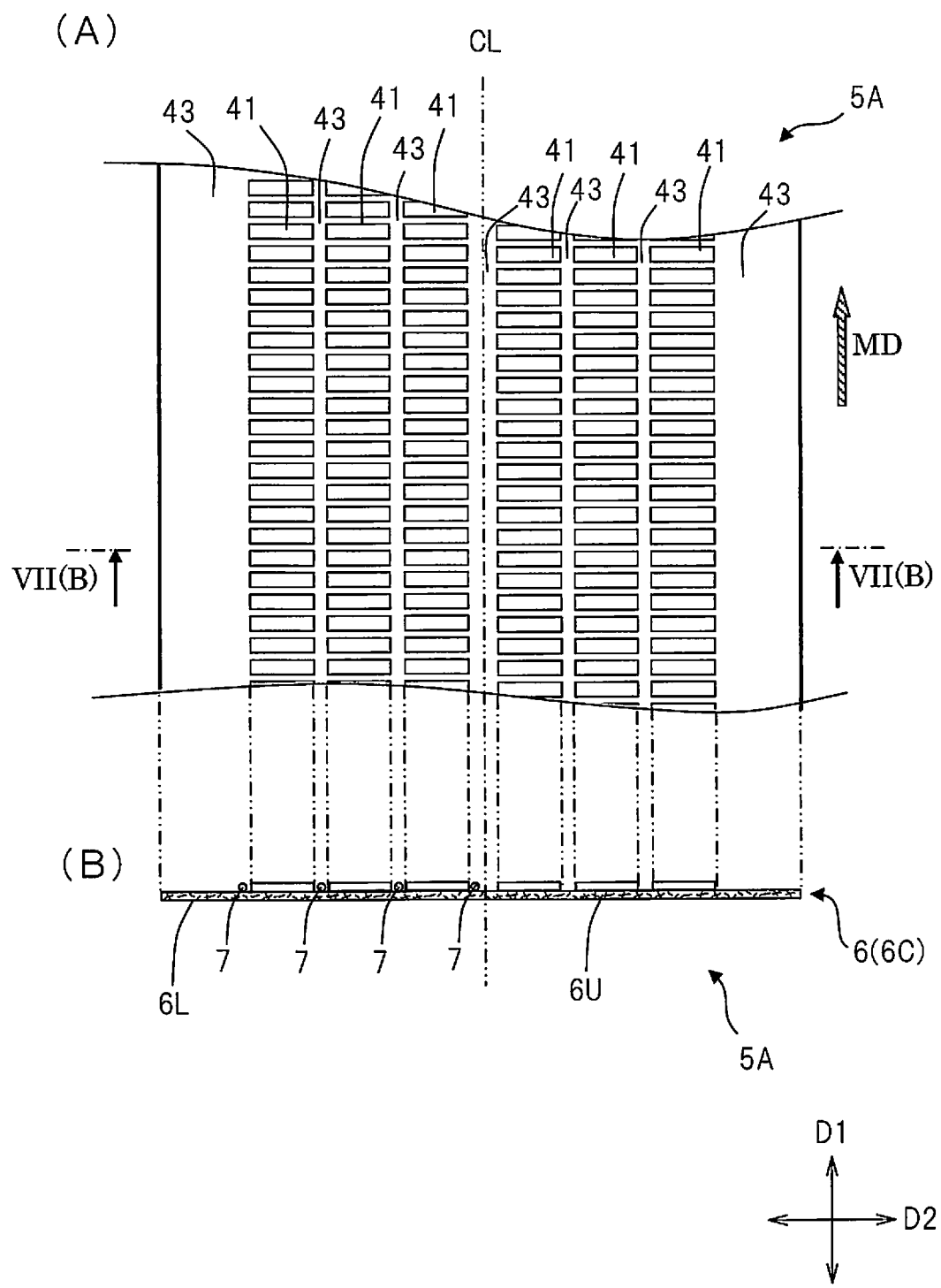
FIG. 7 is a front view and cross-sectional view of a composite stretchable member before folding over one nonwoven fabric sheet part by the folding device.

Next, the composite stretchable member 5A in the state of FIG. 7 is transferred to a folding device 23. In the example, the folding device 23 is a "rollup sailor". The "rollup sailor" folds the composite stretchable member 5A about a centerline CL (FIG. 7) as the fold line and superposes one side part 6U of the nonwoven fabric sheet 6 over the other side part 6L so that their non-shaped regions 43 are aligned with each other. Therefore, their convex-concave regions 41 are also aligned with each other. As a result, when the composite stretchable member 5A in the state of FIG. 7 passes through the folding device 23, it becomes the composite stretchable member 5B in the state of FIG. 8.

In this example, the folding device 23 folds the member along the centerline CL, but it may also fold the member about any position in accordance with needs so long as along a fold line parallel to the non-shaped regions 43. In this case, the member may be folded about two fold lines.

Furthermore, in this example, the composite stretchable member 5 is produced by superposing two nonwoven fabric sheet parts 6U and 6L of a single nonwoven fabric sheet 6. In another example, two nonwoven fabric sheets 6 may also be shaped separately as explained above and then the nonwoven fabric sheets superposed.

Returning to FIG. 3, finally, the composite stretchable member 5B which passes through the folding device 23 is transported to a bonding press 25 where pressure is applied in the thickness direction DT. Due to this, the nonwoven fabric sheet parts 6U and 6L are joined at the non-shaped regions 43 through the elastic members 7 and the final composite stretchable member 5C is completed.

As described above, in this example, the nonwoven fabric sheet parts 6U and 6L are joined at the non-shaped regions 43 through the elastic members 7. However, in another example, the nonwoven fabric sheet parts 6U and 6L are at least partially joined at the convex-concave regions 41 through the elastic members 7.

In this example, for the nonwoven fabric sheet 6, a basis weight 15 g/m$^2$ SMS nonwoven fabric is used. However, the present invention is not limited to this. As the nonwoven fabric to be used, spun bond nonwoven fabric, melt blown nonwoven fabric, heat roll nonwoven fabric, a SMS nonwoven fabric comprised of a spun bond nonwoven fabric and a melt blown nonwoven fabric combined, air-through nonwoven fabric, spunlace nonwoven fabric, air-laid nonwoven fabric, etc., can be used. Further, as the material of the nonwoven fabric sheet, polyethylene, polypropylene, polyester, acryl, etc., can be used.

For the nonwoven fabric sheet 6, a filament nonwoven fabric which is formed by directly spinning without cutting the fibers, for example, SMS nonwoven fabric or spun bond nonwoven fabric etc., is preferably used. This is because, from the viewpoint of the resistance to a drop in the strength of the nonwoven fabric sheet which is required for shaping treatment, it is possible to make a fabric with a high elongation and with a greater thinness and higher flatness when compared with a staple fiber nonwoven fabric used for the nonwoven fabric sheet 6 itself.

Further, in the example, for the elastic members 7, Lycra® 470dtex is used. However, the present invention is not limited to this. As the elastic members 7, urethane spandex or other elastic yarn can be used. It is preferable to use a plurality of elastic yarns with a denier of 30 to 1500 dtex or so and to use elastic yarns with the same denier or mutually different denier. This is because if less than 30 dtex, the number of elastic yarns used per unit width may increase and the production facility becomes larger, while if more than 1500 Dtex, the interval between the adjoining elastic yarns may become larger and the intermeshing of the upper and lower nonwoven fabric sheet parts 6U and 6L is liable to become uneven. Further, as the material of the elastic members 7, styrene-butadiene, butadiene, isoprene, neoprene, or another synthetic rubber, natural rubber, EVA, SIS, SEBS, SEPS, elastic polyolefin, polyurethane, etc., can be used.

From here, the configuration of the composite stretchable member 5 which is produced by the above method of production will be explained.

Figure 8:
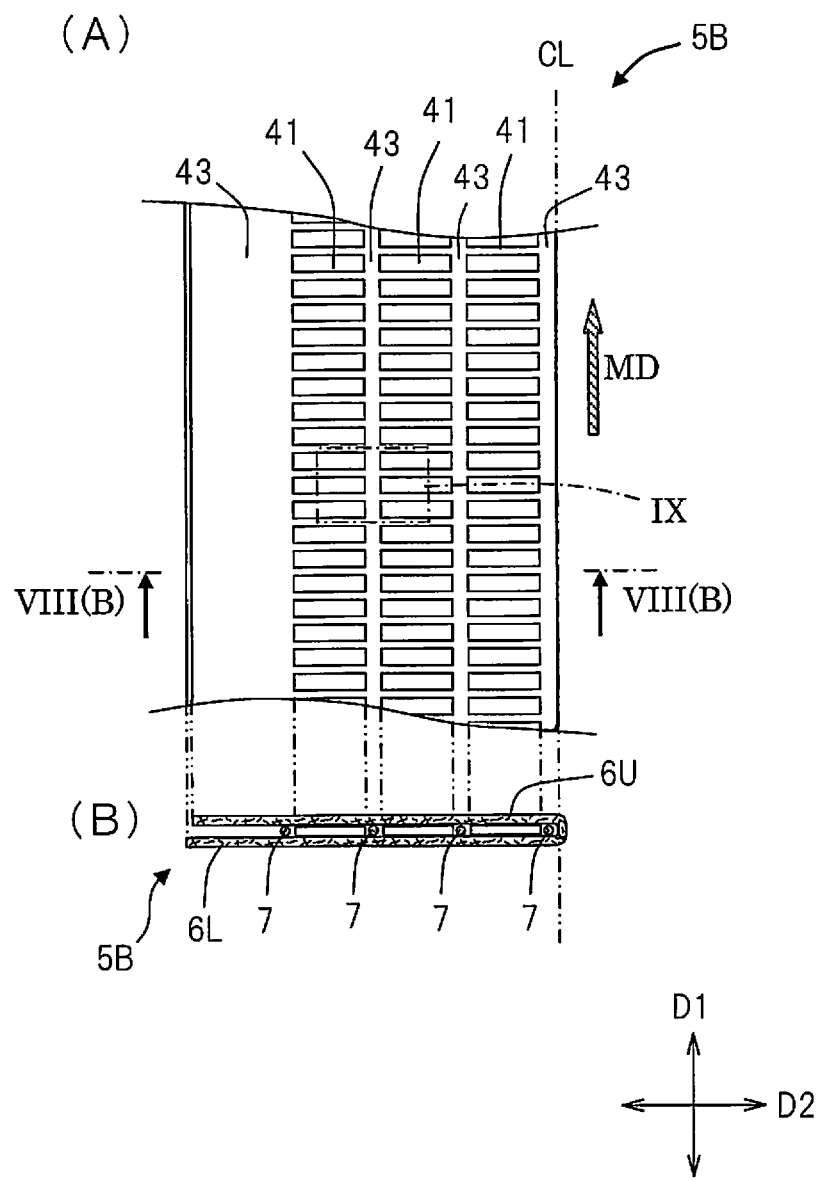
FIG. 8 is a front view and cross-sectional view of a composite stretchable member after folding over one nonwoven fabric sheet part by the folding device.
Figure 9:
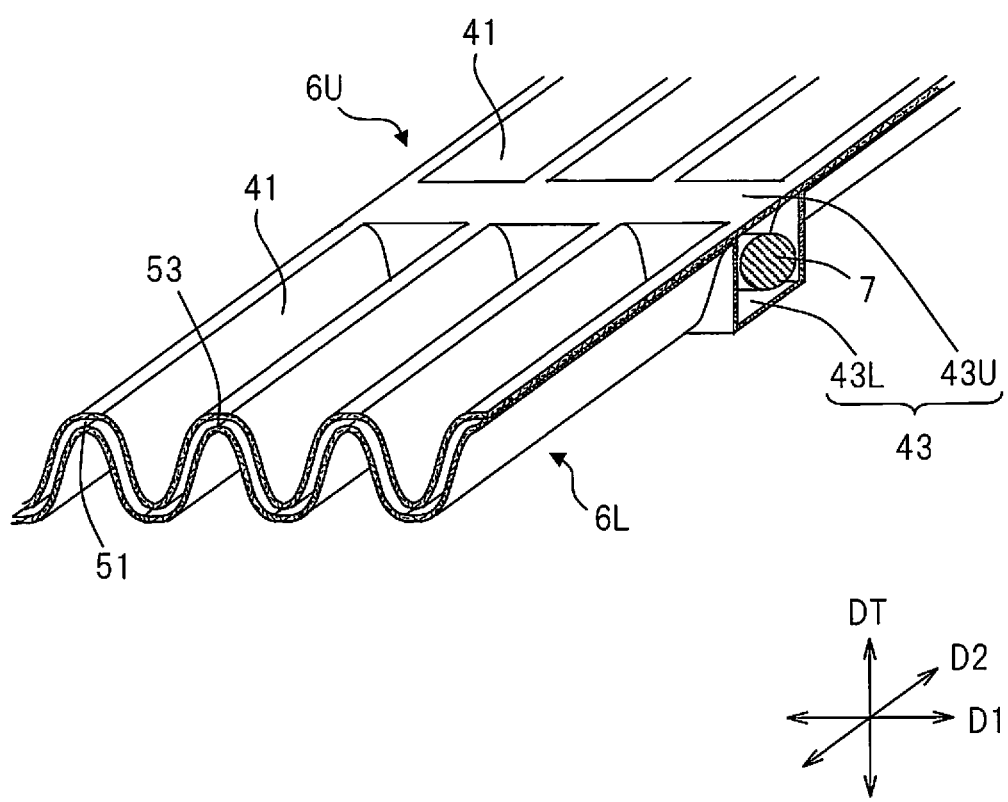
FIG. 9 is a cross-sectional partial enlarged perspective view of a line IX part in FIG. 8.

FIG. 9 is a cross-sectional partial enlarged perspective view of a part IX in FIG. 8, while FIG. 10 is an exploded view of FIG. 9. Referring to FIG. 9 and FIG. 10, the composite stretchable member 5 is comprised of a mutually overlaid upper nonwoven fabric sheet part 6U and lower nonwoven fabric sheet part 6L and an elastic material 7 which is arranged between these nonwoven fabric sheet parts. The upper nonwoven fabric sheet part 6U and lower nonwoven fabric sheet part 6L are formed with the plurality of convex-concave regions 41 which extend straight substantially in parallel with each other in the first direction D1 so that the convex-concave regions 41 are separated by the non-shaped regions 43 in the second direction D2.

The convex-concave regions 41 respectively include concave parts 51 and convex parts 53 which are alternately repeatedly formed in the first direction D1. Specifically, at the convex-concave regions 41, the convex parts 53L of the lower nonwoven fabric sheet part 6L enter into the concave parts 51U of the upper nonwoven fabric sheet part 6U, whereas the convex parts 53U of the upper nonwoven fabric sheet part 6U enter into the concave parts 51L of the lower nonwoven fabric sheet part 6L. Therefore, the convex-concave regions 41 of the upper nonwoven fabric sheet part 6U and the lower nonwoven fabric sheet part 6L adjoin each other. To the contrary, the non-shaped regions 43 which are formed at the upper nonwoven fabric sheet part 6U and the lower nonwoven fabric sheet part 6L are separated from each other in the thickness direction DT.

Figure 11:
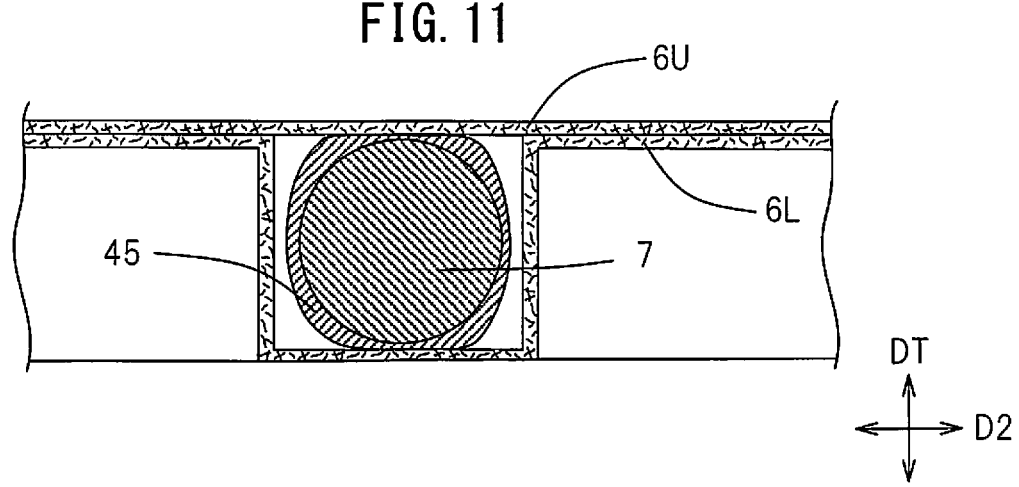
FIG. 11 is a front view of FIG. 9 which enlarges the area around a cross-section of an elastic member.

FIG. 11 is a front view of FIG. 9 which enlarges the area around a cross-section of an elastic member 7. Referring to FIG. 11, it can be understood that two nonwoven fabric sheet parts 6U and 6L are joined with each other at the non-shaped regions 43U and 43L through elastic members 7 by an adhesive, more strictly speaking, are joined with each other at the adhesive part 45 formed by adhesive which is applied at the adhesive applying part 19. Note that, referring to FIG. 11, in this example, the adhesive part 45 is spread to cover the entire circumference of the elastic members 7. In another example, the adhesive is applied only at the locations where the adhesive elastic members 7 and the non-shaped regions 43U and 43L are joined.

Figure 12A:
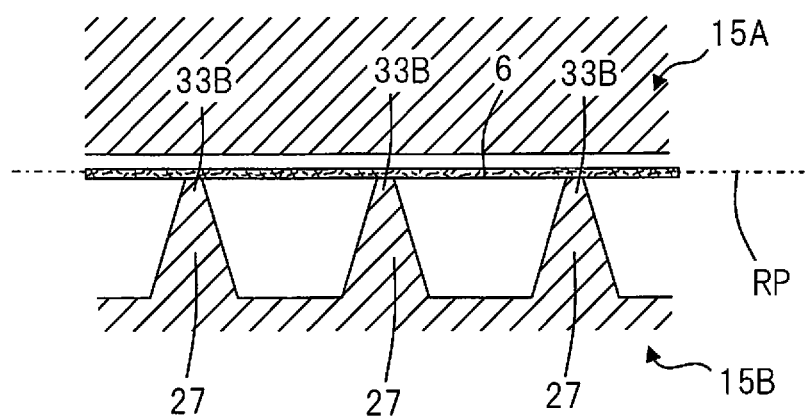
FIG. 12A is an enlarged cross-sectional view of the area around an intermeshing part of a discontinuous gear roll and continuous gear roll as well as a nonwoven fabric sheet which is arranged and deformed between them at the discontinuous parts of the discontinuous gear roll when laying out the discontinuous gear roll and continuous gear roll with their circumferential directions straight.
Figure 12B:
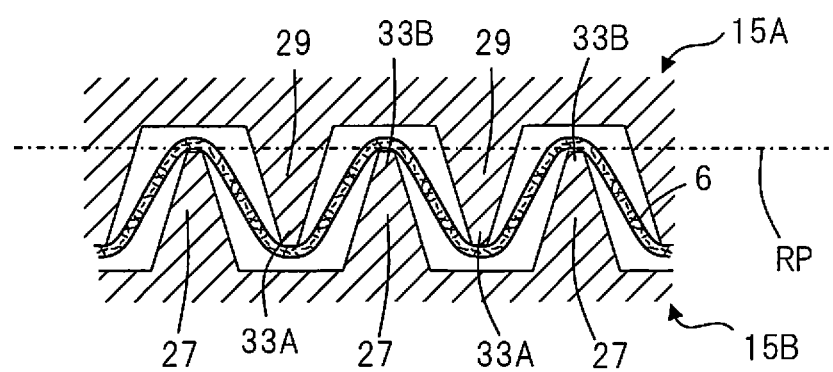
FIG. 12B is an enlarged cross-sectional view of the area around an intermeshing part of a discontinuous gear roll and continuous gear roll as well as a nonwoven fabric sheet which is arranged and deformed between them at discontinuous parts of the discontinuous gear roll when laying out the discontinuous gear roll and continuous gear roll with their circumferential directions straight.

Here, the mechanism by which the nonwoven fabric sheet parts 6U and 6L are deformed to the shapes such as shown in FIG. 9 and FIG. 10 will be explained. FIG. 12A and FIG. 12B are enlarged cross-sectional views, laying open the circumferential directions of the discontinuous gear roll 15A and continuous gear roll 15B straight, of areas around intermeshing parts of the discontinuous gear roll 15A and the continuous gear roll 15B as well as a nonwoven fabric sheet 1 which is arranged between these and deformed. FIG. 12A is a cross-sectional view at a discontinuous part 31 of the discontinuous gear roll 15A, while FIG. 12B is a cross-sectional view at discontinuous teeth 29 of the discontinuous gear roll 15A.

Referring to FIG. 12A and FIG. 12B, on the one hand, as shown in FIG. 12A, the nonwoven fabric sheet 6 which is introduced to the discontinuous parts 31 of the discontinuous gear roll 15A is pushed against the continuous gear roll 15B to the outside in the radial direction of the continuous gear roll 15B, but does not deform and thereby forms the non-shaped regions 43. On the other hand, as shown in FIG. 12B, the nonwoven fabric sheet 6 which is caught between the discontinuous teeth 29 of the discontinuous gear roll 15A and the continuous teeth 27 of the continuous gear roll 15B are locked at the tooth front end parts 33. By doing this, the nonwoven fabric sheet 6 is stretched between each tooth front end part 33B, tooth front end part 33A and other tooth front end parts 33B which adjoin each other in a manner of the three-point bending whereby convex parts 53, of which top parts are formed at the tooth front end parts 33A, are formed.

Furthermore, the nonwoven fabric sheet 6 is stretched between each tooth front end part 33A and tooth front end part 33B and other tooth front end parts 33A which adjoin each other in a manner of the three-point bending whereby concave parts 53, of which bottom parts are formed at the tooth front end parts 33B, are formed. At this time, the non-shaped regions 43 of the nonwoven fabric sheet 6 which are pushed against the continuous gear roll 15B at the discontinuous parts 31 of the discontinuous gear roll 15A and the bottom parts of the concave parts 51 of the nonwoven fabric sheet 6 to be locked at the tooth front end parts 33B of the continuous gear roll 15B at the discontinuous tooth 29 of the discontinuous gear roll 15A become substantially the same in positions in the radial directions of the gear rolls 15A and 15B. That is, the thickness of the nonwoven fabric sheet 6 becomes substantially the same. Accordingly, even after the nonwoven fabric sheet 6 is formed with convex-concave regions 41 and non-shaped regions 43, these are present on substantially the same plane. Here, that plane is defined as the virtual reference plane RP for the nonwoven fabric sheet parts 6U and 6L. Here, the reference plane RP is flat, and the non-shaped regions 43 extend over this reference plane RP. Note that, the nonwoven fabric sheet parts 6U and 6L are flexible, so the reference plane RP does not necessarily have to be flat.

Therefore, speaking in terms of the relationship between the convex parts 53 and the reference plane RP, the convex parts 53 stick out from the reference plane RP, that is, from the non-shaped regions 43 in terms of the thickness direction. Further, the concave parts 51 reach the convex-concave regions 41 between two adjoining convex parts 53.

Furthermore, here, the mechanism by which the convex parts 52 enter into the concave parts 51 in the above process of manufacture will be explained.

Referring to FIG. 9, it can be understood that the reference planes RP of the upper side nonwoven fabric sheet 6U and the lower side nonwoven fabric sheet 6L are separated by the amount by which the convex parts 53 stick out from the reference planes RP. That is, the non-shaped regions 43U and 43L of the upper nonwoven fabric sheet 6U and the lower nonwoven fabric sheet 6L which face each other are separated from each other. This is achieved by making one part of the shaping device 15 the discontinuous gear roll 15A and making another the continuous gear roll 15B and thereby making the convex parts 53 stick out from the reference plane RP in only one direction, and by making the surfaces of the nonwoven fabric sheets 6U and 6L at the sides which have the convex parts 53 be superposed so as to face each other and in turn be superposed so that the reference planes RP of the nonwoven fabric sheets 6U and 6L are positioned at different outside planes of the composite stretchable member 5. Therefore, the elastic members 7 which extend at certain intervals in the spaces defined between the non-shaped regions 43U and 43L of the nonwoven fabric sheets 6U and 6L can be placed. In turn, by arranging the elastic members 7 between the nonwoven fabric sheet parts 6U and 6L, the action of the convex parts 53 entering into the concave parts 51 is not prevented.

Furthermore, in the above process of manufacture, the entry of the convex parts 53 into the concave parts 51 can be explained as being due to the following mechanism.

A nonwoven fabric is generally soft and easy to deform, so to transport the nonwoven fabric sheet in the process of manufacture, usually a certain tension is given in the machine direction MD, that is, a first direction D1. In this example, in the above-described process, when folding the nonwoven fabric sheet 6C of the composite stretchable member 5A, the folding device 23 is used.

The nonwoven fabric sheet part 6U is further given tension from the folding device 23 in the first direction D1, when passing through the folding device 23. Specifically, this tension is applied by a "sailor edge" (not shown) of the "rollup sailor" of one specific embodiment of the folding device 23. Due to this, the upper side nonwoven fabric sheet part 6U is stretched in the first direction D1 more than the lower side nonwoven fabric sheet part 6L. In turn, the convex-concave pitch of the convex-concave regions 41 (length of one cycle of concave parts 51 and convex parts 53 in the first direction) of the upper side nonwoven fabric sheet part 6U becomes slightly greater than the convex-concave pitch of the convex-concave regions 41 of the lower side nonwoven fabric sheet part 6L.

After this, when the upper side nonwoven fabric sheet part 6U is superposed on the lower side nonwoven fabric sheet part 6L, the tension is released and the state where the tension which had been applied before introduction into the folding device 23 is applied is returned to. Next, the convex-concave pitch returns to the state before the composite stretchable member 5A was introduced into the folding device 23. Therefore, the concave parts 51U and convex parts 53U of the upper side nonwoven fabric sheet part 6U and the convex parts 53L and concave parts 51L of the lower side nonwoven fabric sheet part 6L change in relative positions. As a result, when the convex-concave pitches of these parts become the same as each other when the tension is released, the shapes of the concave parts 51 and convex parts 53 also help to cause offset by half a pitch to thereby make the convex parts 53 enter into the concave parts 51.

Note that, in this composite stretchable member 5, by the nonwoven fabric sheet 6 being stretched in the thickness direction DT at the convex-concave regions 41, in the contracted state, the thickness of the composite stretchable member 5 at the convex-concave regions 41 becomes thicker than the thickness at the non-shaped regions 43. Therefore, the feel when the wearer contacts the composite stretchable member 5 is good. This is because the non-shaped regions 43 which become harder due to the adhesive coated around the elastic members 7 are prevented from sticking out from the convex-concave regions 41 and the non-shaped regions 43 are prevented from contacting the body of the wearer before the convex-concave regions 41 and causing the wearer to feel uncomfortable. For similar reasons, it is more preferable that the diameter of the elastic members 7 is slightly smaller than the gap between aligned non-shaped regions 43.

In the above, the method of production in the case of use of the folding device 23 was explained. In another example, two nonwoven fabric sheets are separately shaped to the same shapes and superposed to produce the above-mentioned such composite stretchable member 5 without using a folding device 23. In this case, when superposing nonwoven fabric sheets together, one nonwoven fabric sheet is applied higher tension than another nonwoven fabric sheet in a first direction. Due to this, it is possible to adopt the same configuration as the case of superposing two nonwoven fabric sheet parts 6U and 6L of a single nonwoven fabric sheet 6. Due to the above-mentioned reason, the convex parts 53U and 53L of the nonwoven fabric sheet parts 6U and 6L enter into the concave parts 51L and 51U of the nonwoven fabric sheet parts 6L and 6U. However, when the two nonwoven fabric sheets differ from each other in basis weight, thickness of fibers, etc., note that it is necessary to adjust the tensions which are applied to the nonwoven fabric sheets as to make the convex-concave pitches match.

In this regard, as explained at the start in the description relating to the first embodiment, the disposable diaper 1 of the first embodiment is provided with the composite stretchable member 5 which is produced using the above-mentioned method of production as side panels 5S so as to match with the size of the disposable diaper 1. At this time, in the first embodiment, the composite stretchable member 5 is joined with the absorbent element 3 so that the first direction D1 of the composite stretchable member 5 is substantially aligned with the transverse direction L of the disposable diaper 1 and so that the second direction D2 of the composite stretchable member 5 is substantially aligned with the longitudinal direction T of the disposable diaper 1.

As explained at the start in the Description, when putting a pants type of disposable diaper 1 on a wearer, the legs of the wearer contact the waist part WP (FIG. 1), in particular the side parts WPE of the waist part (FIG. 1), whereby force acts on these parts in the direction of passage of the legs of the wearer and in turn in particular in the longitudinal direction T. In the disposable diaper 1 of the first embodiment, the composite stretchable member 5 is arranged at the side parts WPE in the waist part WP.

From here, a mechanism enabling the disposable diaper 1 of the first embodiment to be put on easier compared with the conventional one will be explained.

As explained above, the composite stretchable member 5 has the convex-concave regions 41 shaped with concave parts 51 and convex parts 53 alternately formed in a first direction. As will be understood from the cross-section of the front side of FIG. 9, the cross-section of a convex-concave region 41 along the first direction has a wavy shape. This shape acts as a center core of a cross-sectional wavy shape arranged at the inside of a general cardboard. Furthermore, the convex-concave regions 41 of two nonwoven fabric sheet parts 6U and 6L adjoin each other. More specifically, the convex parts 53U and 53L of the nonwoven fabric sheet parts 6U and 6L enter into the concave parts 51L and 51U of the nonwoven fabric sheet parts 6L and 6U, so two nonwoven fabric sheet parts 6U and 6L cooperate to support each other. As a result, the composite stretchable member 5 has a rigidity with respect to compressive force in the second direction D2 and in turn the longitudinal direction T of the disposable diaper 1 which is higher than a composite stretchable member 5' which is formed from two not shaped nonwoven fabric sheet parts 6'.

Figure 13A:
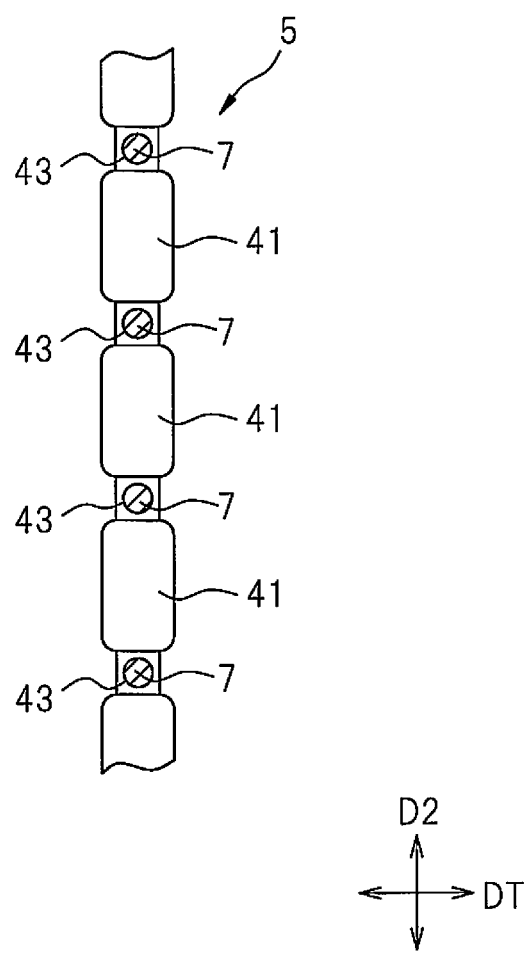
FIG. 13A is a diagram which shows one example of a shape of the composite stretchable member of the first embodiment before compressed in a second direction.
Figure 13B:
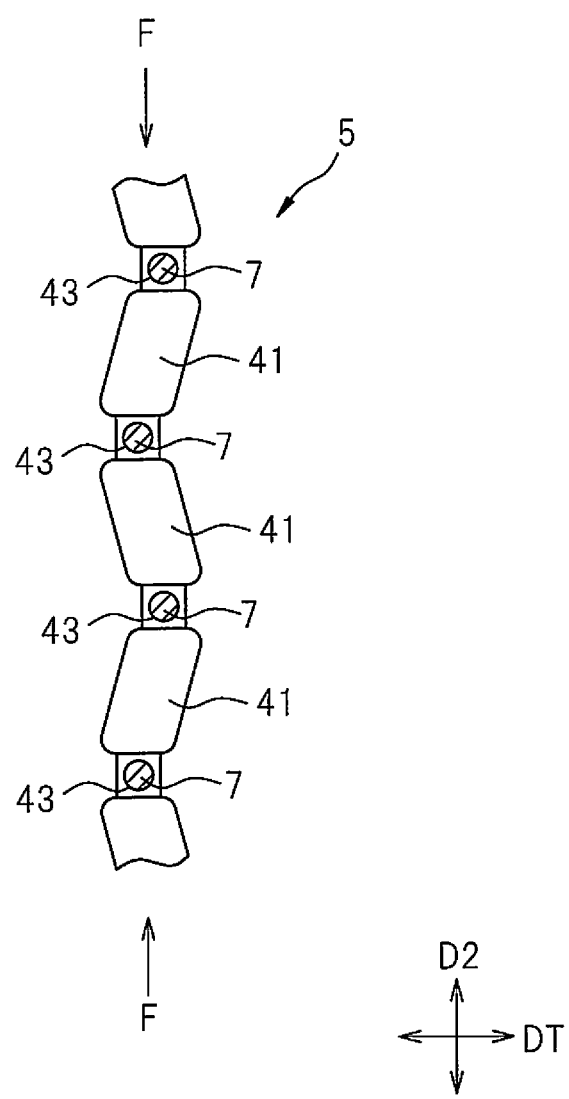
FIG. 13B is a diagram which shows one example of a shape of the composite stretchable member of the first embodiment after compressed in a second direction.
Figure 14A:
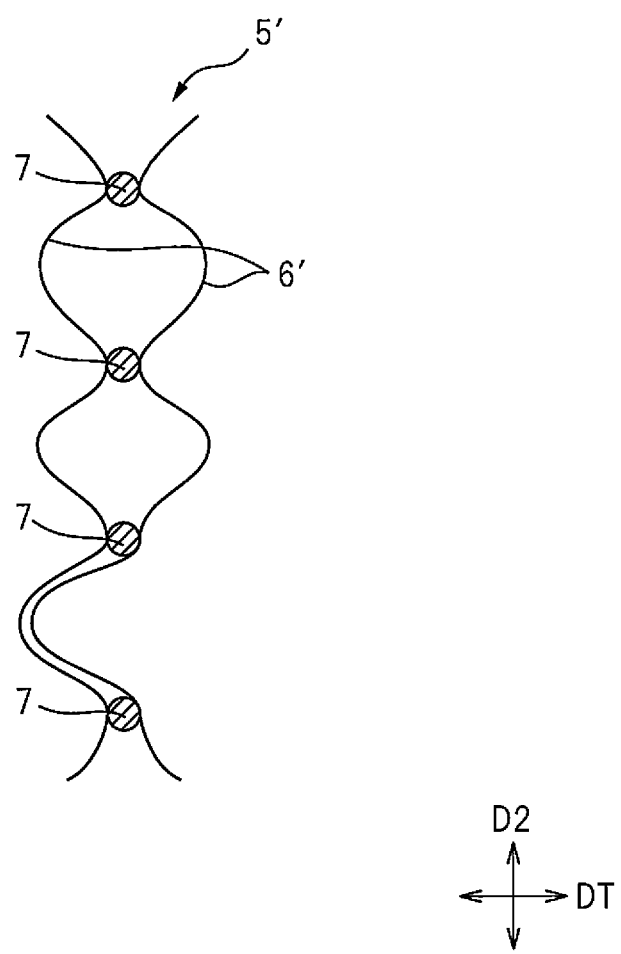
FIG. 14A is a diagram which shows one example of a shape of a composite stretchable member which is formed from two not shaped nonwoven fabric sheet parts before compressed in a second direction.
Figure 14B:
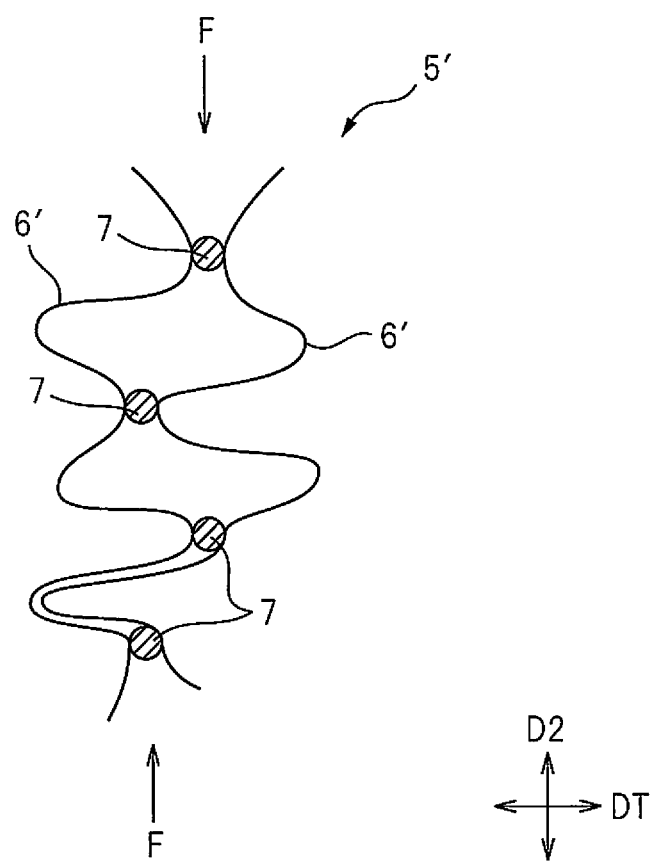
FIG. 14B is a diagram which shows one example of a shape of a composite stretchable member which is formed from two not shaped nonwoven fabric sheet parts after compressed in a second direction.

FIG. 13A and FIG. 13B are diagrams which show examples of the shapes before and after the composite stretchable member 5 is compressed in the second direction. Further, FIG. 14A and FIG. 14B are diagrams which show examples of the shapes before and after the composite stretchable member 5' which is formed from two not shaped nonwoven fabric sheet parts 6' is compressed in the second direction. The composite stretchable member 5 becomes harder to bend between the elastic members 7, that is, become harder to buckle, even when compressive force is applied in the second direction, at the convex-concave regions 41 due to the compressive rigidity which is due to the shape imparted and the configuration. Referring to FIG. 13B, the state is shown where this composite stretchable member 5 is not bent at the convex-concave regions 41 and is somewhat bent at the non-shaped regions 43. As opposed to this, referring to FIG. 14B, in the not shaped composite stretchable member 5', when compressive force is given in the second direction, the nonwoven fabric sheet part 6' which is positioned between the elastic members 7 freely move without generating any force due to the shape, so the pitch between elastic members 7 becomes shorter. Along with this, the nonwoven fabric sheet part 6' sticks out in the thickness direction, so in the not shaped composite stretchable member 5', large pleats are easily formed. Accordingly, it can be understood that the composite stretchable member 5 has a higher compressive strength in the second direction D2 than the conventional composite stretchable member 5'. As a result, the disposable diaper 1 of the first embodiment is resistant to the formation of large pleats liable to catch the legs of the wearer in the process of passage of the legs of the wearer from the waist opening WO to the leg openings LO when putting the diaper on. Furthermore, the force in the longitudinal direction T which is applied when putting the disposable diaper 1 on a wearer becomes easily transmitted. Accordingly, the disposable diaper 1 of the first embodiment is more easily put on than a conventional disposable diaper.

Furthermore, the compressive strength test explained below was performed in order to confirm the high compressive rigidity of the composite stretchable member 5.

Test Method

Figure 15A:
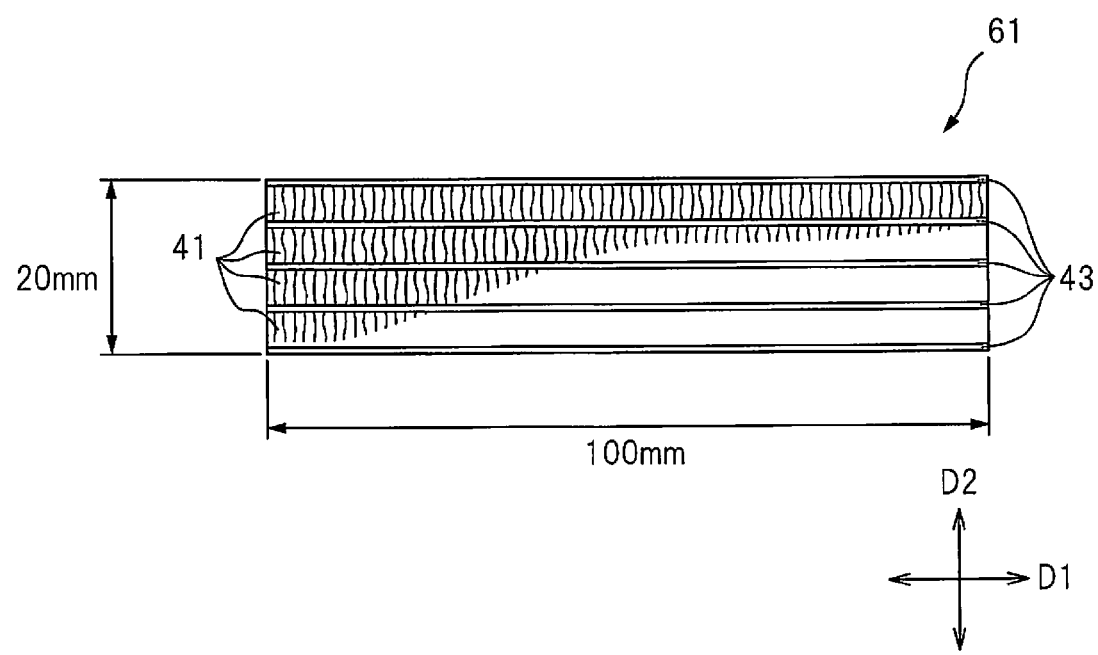
FIG. 15A is a view which explains a size of a test piece of a compressive strength test.
Figure 15B:
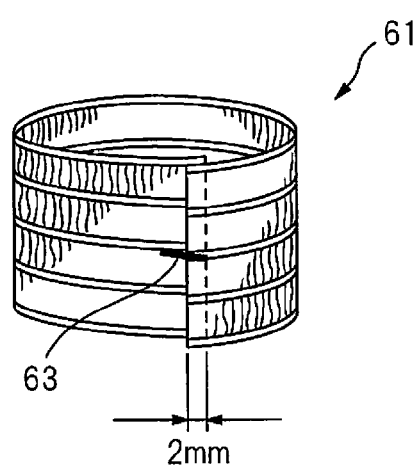
FIG. 15B is a schematic perspective view of a test piece of a compressive strength test.

The compressive strength test which is performed for this purpose is a test similar to the ring crush test (JIS P8126) which is used for a compressive strength test for papers and paperboards. In this compressive strength test, as shown in FIG. 15A, a test piece 61 of a shape of a length of 100 mm in a first direction and 20 mm in a second direction is prepared. Next, the test piece 61, as shown in FIG. 15B, is formed into a ring and the end parts are joined together at 2 mm overlapping parts by a stapler (FIG. 15B shows a staple 63.) at just one location at the approximate center.

Figure 16:
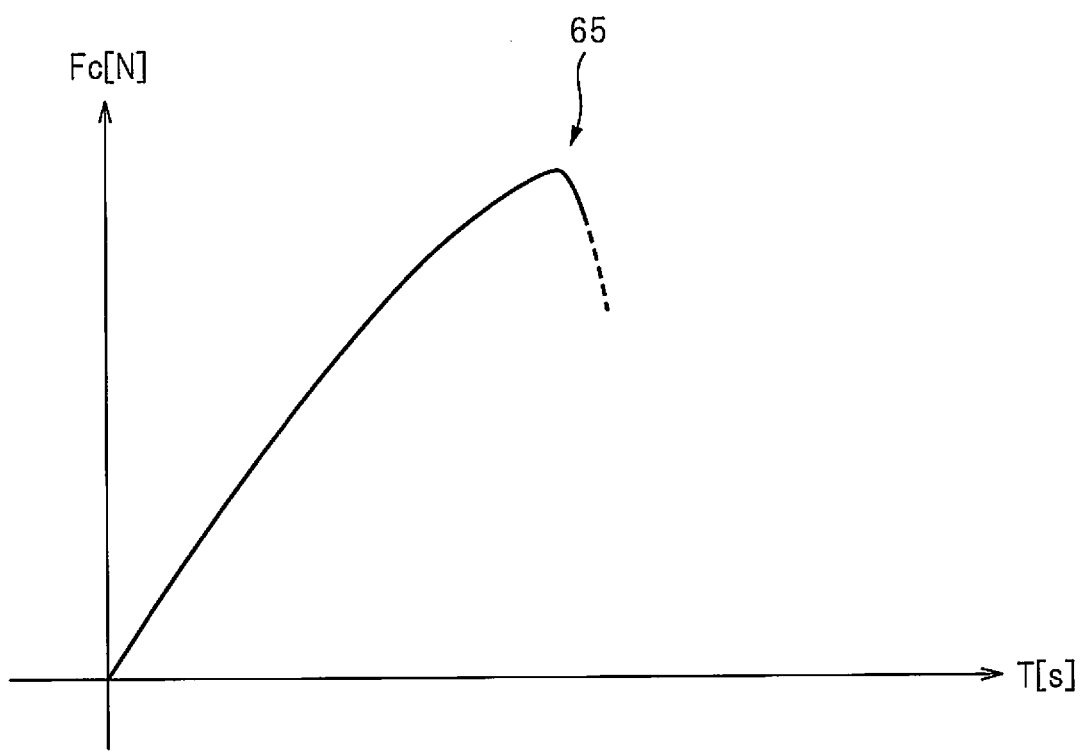
FIG. 16 is a graph which shows one example of the trends in time and compressive force in a compressive strength test.

To carry out this compressive strength test, this test piece 61 is placed on a test table and a compressive force is applied to the upper edge part as a whole of the test piece 61 downward in the vertical direction until the test piece 61 buckles. FIG. 16 is a graph which shows one example of the trends in the time T[s] and compressive force Fc[N] in a compressive strength test. Referring to FIG. 16, it can be understood that the test piece 61 is gradually given a compressive force, then, at the time indicated by reference numeral 65 in FIG. 16, the test piece 61 can no longer withstand the compressive force and buckles. The compressive force which had been applied at the time when the piece buckles is used as an evaluation criterion of the compressive strength test.

The samples which are shown below were tested by this compressive strength test.

Example

The test piece 61 of the example was formed from a composite stretchable member 5 which was produced by the above method of production. The test piece 61 of the example which has the same size as the above-mentioned test piece 61 was used. In the test piece 61 of the example, the pitch between elastic members 7 was 5 mm. A basis weight 15 g/m² SMS nonwoven fabric was used.

Comparative Example

Except for using a not shaped nonwoven fabric sheet part 6', a composite stretchable member 5' which was formed in the same way as the composite stretchable member 5 and made the size of the above-mentioned test piece 61 was used.

Below, the results of the compressive strength test will be shown. Note that, the following measurement results are mean values of measurement results of three test pieces of the example and comparative example.

TABLE 1

|  | Example | Comparative Example |
| --- | --- | --- |
| Compressive strength (N) | 0.58 | 0.39 |

As shown in Table 1, it was confirmed that the composite stretchable member 5 of the first embodiment has a sufficiently higher compressive strength in the second direction compared with a not shaped conventional composite stretchable member.

Further, the composite stretchable member 5 of the first embodiment had a thickness measured by a measuring device of 2.0 mm or less when applying a pressure of 3 gf/cm² (0.3 kPa) in the thickness direction to the composite stretchable member in the 50% stretched state.

Furthermore, the composite stretchable member 5 of the first embodiment has a density D of the profile curve elements in a 50% stretched state is 15/cm.

Figure 17:
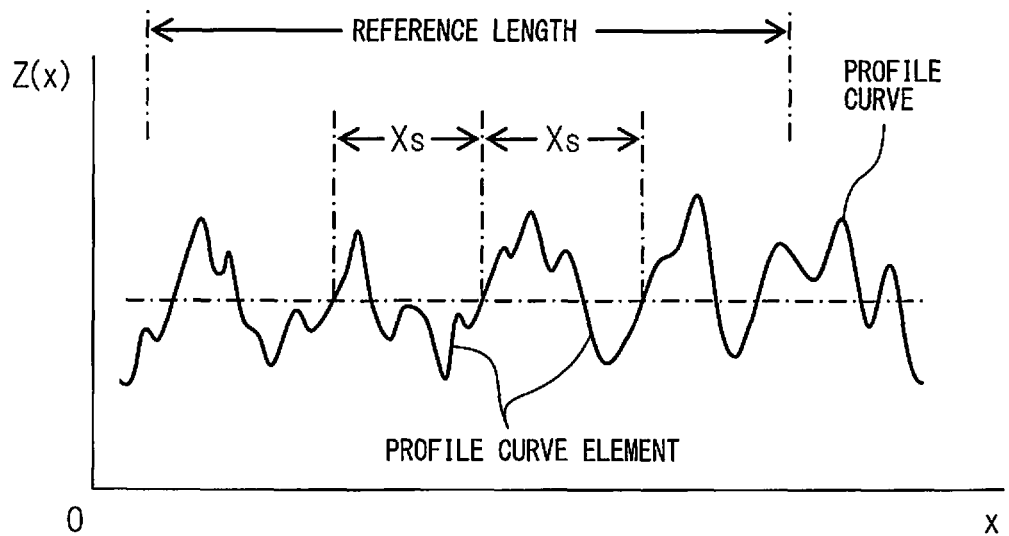
FIG. 17 is a graph to explain the height and length with an example of a profile curve.

Here, the above-mentioned 50% stretched state indicates the state where the composite stretchable member is made to stretch in the stretch direction to give a stretch rate of 50%. The stretch rate is defined as below:

Stretch rate (%)=$(LM-LM0)/LM0 \cdot 100$ where, LM: stretch direction length of stretched composite stretchable member part LM0: stretch direction length of the composite stretchable member part in natural state The above-mentioned density D of profile curve elements is found as follows: First, the profile curve along the stretch direction at the convex-concave regions 41 of the composite stretchable member 5 is measured by a shape measuring device. Note that, the cross-sectional shape is preferably measured at the substantial center between two adjoining elastic members. Next, from this profile curve, the height Z(x) and length Xs of the profile curve elements at the reference length are found (see JIS B0601:2001 (ISO4287: 1997), JIS B0651:2001 (ISO3274:1996), and FIG. 17). Finally, the density D of profile curve elements is calculated from the mean value PSm of the length Xs of the above-mentioned profile curve elements (D=1/PSm).

As explained above, the composite stretchable member 5 of the first embodiment has a thickness measured by a measuring device of 2.0 mm or less when applying a pressure of 3 gf/cm$^2$ (0.3 kPa) in the thickness direction to the composite stretchable member in the 50% stretched state. Therefore, this composite stretchable member 5 is sufficiently thin and free of large pleats and in turn the disposable diaper 1 can be easily put on the wearer. However, the composite stretchable member of another embodiment has a thickness more than 2.0 mm.

Further, as explained above, the composite stretchable member 5 of the first embodiment further has a density D of profile curve elements in the 50% stretched state of 8 to 15/cm. Therefore, there is provided a composite stretchable member which has more uniform pleats and in turn is thin overall and smoother on the surface even when in the contracted state. Due to this, a composite stretchable member which has a more excellent feel and aesthetic appearance is provided. Furthermore, the pleats are not excessively small, so production of the composite stretchable member is easy. However, the composite stretchable member of another embodiment has a density D of the profile curve elements of less than 8/cm. Furthermore, the composite stretchable member of another embodiment has a density D of the profile curve elements of greater than 15/cm.

Summarizing the above descriptions, according to the disposable diaper 1 of the first embodiment, the following technical advantages can be achieved.

(1) The composite stretchable member 5 which is produced by the above-mentioned method is arranged at the waist side parts WPE of the disposable diaper 1 where the legs of the wearer are most easily caught. Therefore, large pleats like with a conventional disposable diaper are not formed and, furthermore, force in the longitudinal direction T which is applied when putting the disposable diaper 1 on the wearer is easily transmitted, so the disposable diaper 1 can be easily put on the wearer.

(2) Further, the composite stretchable member 5 preferably has a more superior feel from the viewpoint of contact with the skin of the wearer. As explained above, the thickness of the composite stretchable member 5 in the contracted state is greater at the convex-concave region 41 than the non-shaped region 43. Therefore, the non-shaped regions 43, which become hard due to the adhesive which is applied around the elastic members 7, do not directly contact the skin of the wearer. As a result, the feel when contacting the composite stretchable member 5 is good.

(3) Further, from the viewpoint of being visible from the outside, the composite stretchable member 5 preferably has a more excellent aesthetic appearance. Due to the configuration of the composite stretchable member 5 of the convex parts 53 entering into the concave parts 51, it is possible to form regular pleats as formed even in the contracted state. Due to this, it is possible to produce a composite stretchable member 5 which is thinner overall and which is smooth on the surface, so it becomes easy for the legs of the wearer to slide on the surface when putting on the diaper and in turn easy to put the disposable diaper 1 on the wearer.

(4) Further, since a filament nonwoven fabric is used as the material of the composite stretchable member 5, it is possible to form a composite stretchable member 5 which is thinner and higher in flatness than when using a staple fiber nonwoven fabric as the material. Therefore, it is further easy to pass the legs through the disposable diaper 1 and easy to put the disposable diaper 1 on the wearer.

Second Embodiment

Figure 18:
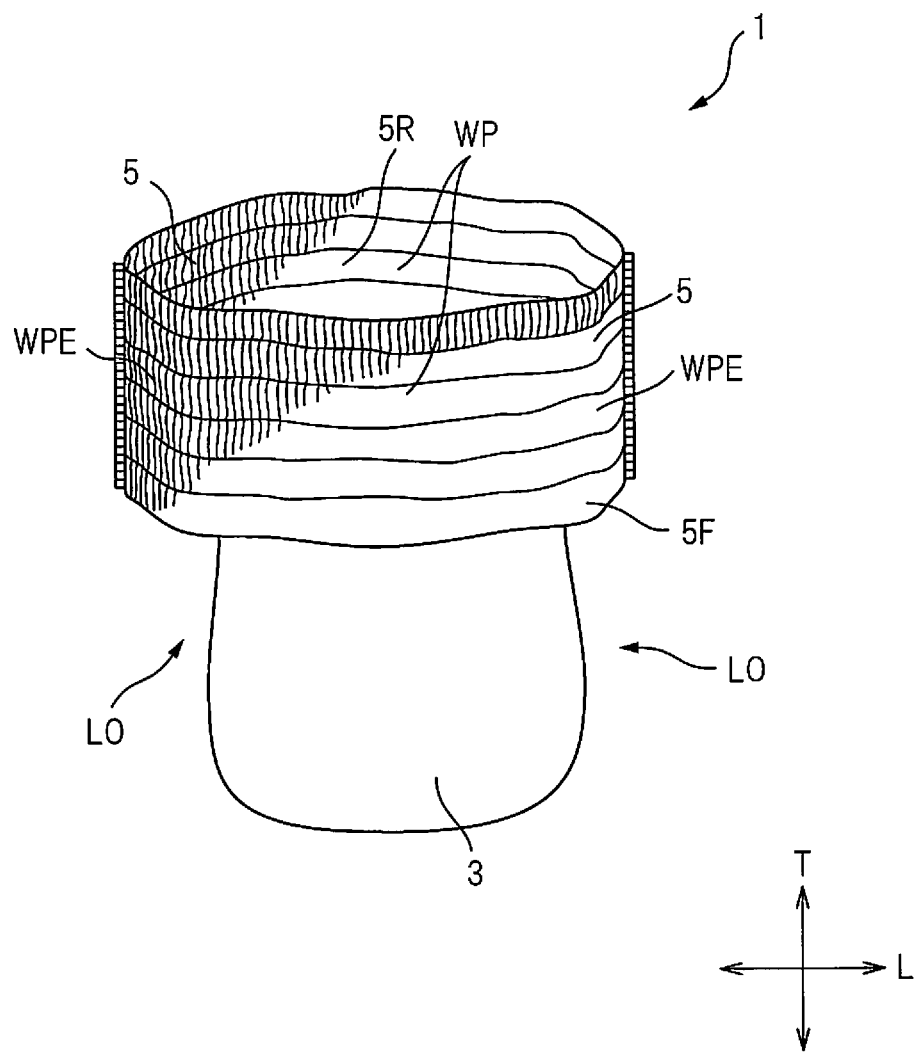
FIG. 18 is a front bird's eye view which shows a disposable diaper of a second embodiment.
Figure 19:
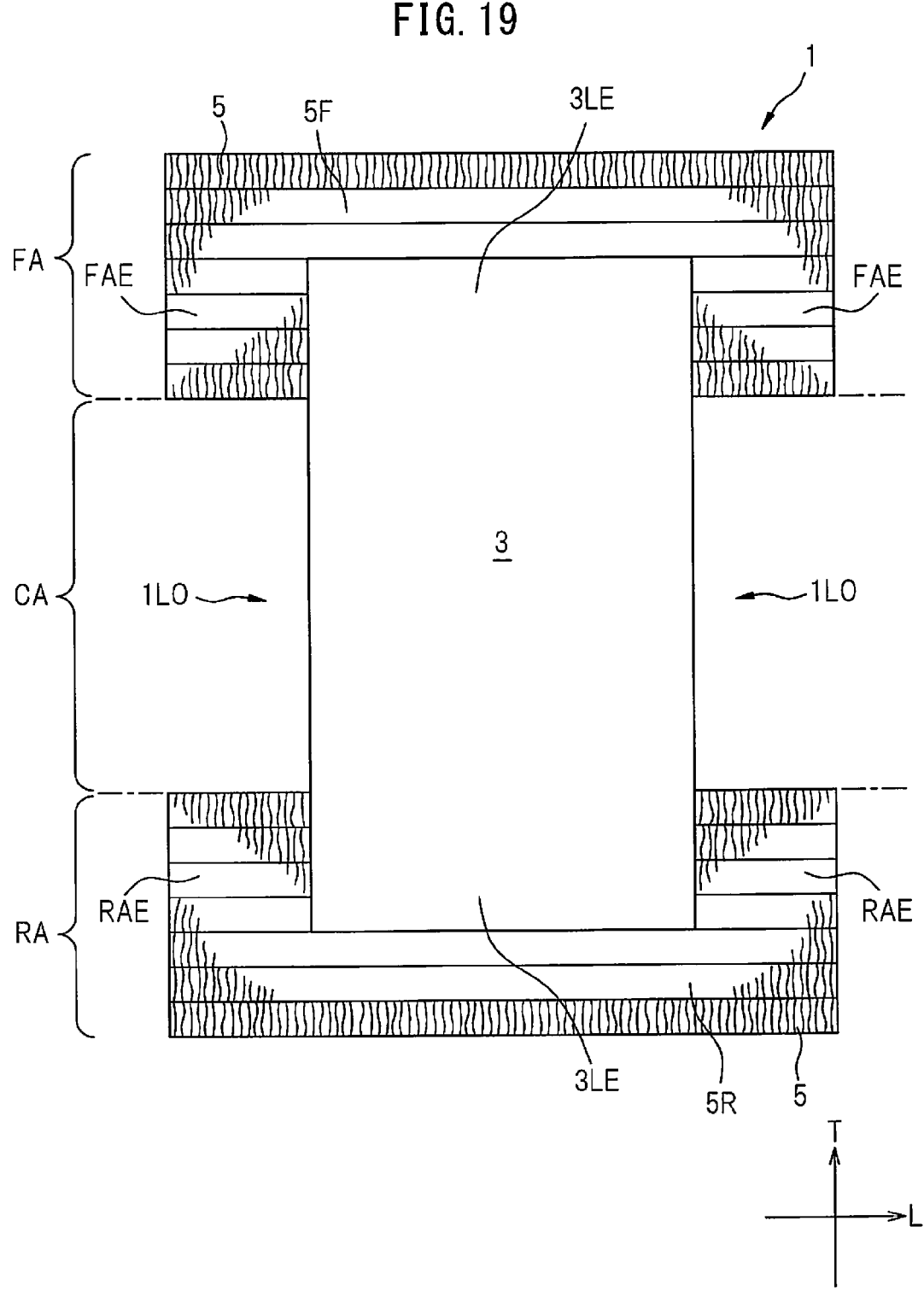
FIG. 19 is a laid open view of a disposable diaper in FIG. 18.

From here, FIG. 18 and FIG. 19 will be used to explain a disposable diaper 1 of a second embodiment. Note that, for the second embodiment, only the differences from the first embodiment will be explained.

FIG. 18 is a front bird's eye view of a disposable diaper 1 of a second embodiment. The disposable diaper 1 of the second embodiment is a so-called "3P" (three-piece) type of diaper. FIG. 19 is a laid open view of a disposable diaper 1 of a second embodiment. This disposable diaper 1 includes at least an absorbent element 3 which is comprised of a top sheet, an absorber, a back sheet, etc., and a substantially rectangular shape front member 5F and rear member 5R which are formed from the composite stretchable member 5.

Referring to FIG. 19, the front member 5F is arranged at the front area FA, while the rear member 5R is arranged at the rear area RA. The front member 5F is joined with one of the longitudinal direction end parts 3LE of the absorbent element 3, while the rear member 5R is joined with the other longitudinal direction end part 3LE of the absorbent element 3. Due to the part of the crotch area CA narrower in width than the front area FA and the rear area RA, leg opening forming parts 1LO which form the leg openings LO is formed.

Referring to FIG. 19, it can be understood that composite stretchable members 5 is provided at the areas including the side edge parts FAE of the front area FA and the side edge parts RAE of the rear area RA. Furthermore, in the second embodiment, the front member 5F which is comprised of a single composite stretchable member 5 extends from one transverse direction end part FAE of the front area FA to the other transverse direction end part FAE of the front area FA. Furthermore, the rear member 5R which is comprised from another composite stretchable member 5 extends from one transverse direction end part RAE of the rear area RA to the other transverse direction end part RAE of the rear area RA.

In the disposable diaper 1 of the second embodiment, the composite stretchable member 5 extends over not only the side parts WPE of the waist part WP of the disposable diaper 1 (FIG. 18), but also from one side part WPE to the other side part WPE of the waist part WP. In other words, in this disposable diaper 1, the composite stretchable member 5 is arranged at the waist part WP (FIG. 18) as a whole, that is, over a broad part which the legs of the wearer may contact when the diaper is put on. Therefore, it is further advantageous that the legs will be prevented from getting caught and the disposable diaper 1 can be easily put on the wearer.

All features which can be understood by a person skilled in the art from the description, drawings, and claims are included independently or further in any combination with one or more of the features which are disclosed here even if these features are explained in combination only in relation to specific other features in this description unless these features are clearly excluded or unless the technical mode would be an impossible or meaningless combination.

The present invention is defined as follows (1) A disposable diaper which is provided with a waist opening and a pair of leg openings, wherein the disposable diaper includes a longitudinal direction and a transverse direction which is perpendicular to the longitudinal direction, a composite stretchable member is provided at least at side parts of a waist part which is positioned between the waist opening and the leg openings of the disposable diaper, the composite stretchable member is provided with a first nonwoven fabric sheet part and a second nonwoven fabric sheet part which are mutually overlaid as well as elastic members which are arranged between the first nonwoven fabric sheet part and the second nonwoven fabric sheet part, each of the first nonwoven fabric sheet part and the second nonwoven fabric sheet part is provided with:

a plurality of convex-concave regions which are provided with convex parts and concave parts which are alternately repeated along the transverse direction and which extend in the longitudinal direction and at least one non-shaped region which separates these convex-concave regions from each other in the longitudinal direction, the first nonwoven fabric sheet part and the second nonwoven fabric sheet part are overlaid so that the convex-concave regions of the first nonwoven fabric sheet part and the second nonwoven fabric sheet part adjoin each other and the non-shaped regions of the first nonwoven fabric sheet part and the second nonwoven fabric sheet part are separated from each other and so that the convex-concave regions and the non-shaped regions are respectively aligned in the longitudinal direction, and the first nonwoven fabric sheet part and the second nonwoven fabric sheet part are joined with each other by an adhesive which is applied to the elastic members.

(2) The disposable diaper according to (1) wherein the elastic members extend between the non-shaped regions which are separated from each other in the longitudinal direction while being aligned with each other.

(3) The disposable diaper according to (1) or (2) wherein the composite stretchable member extends from one side part to the other side part of the waist part.

(4) The disposable diaper according to any one of (1) to (3) wherein the convex parts of the first nonwoven fabric sheet part enter into the concave parts of the second nonwoven fabric sheet part and wherein the convex parts of the second nonwoven fabric sheet part enter into the concave parts of the first nonwoven fabric sheet part.

(5) The disposable diaper according to any one of (1) to (4) wherein the convex parts respectively stick out from the non-shaped regions in terms of the thickness direction, and the concave parts respectively reach the non-shaped regions between two adjoining the convex parts.

(6) The disposable diaper according to any one of (1) to (5) wherein the composite stretchable member is formed from a filament nonwoven fabric.

(7) The disposable diaper according to any one of (1) to (6) wherein the mutually overlapping first nonwoven fabric sheet part and second nonwoven fabric sheet part are formed in a single nonwoven fabric sheet, and the single nonwoven fabric sheet is folded back along a fold line which is parallel in the first direction and overlaid.

REFERENCE SIGNS LIST 1 disposable diaper
5 composite stretchable member
6 nonwoven fabric sheet
6U upper nonwoven fabric sheet part (first or second nonwoven fabric sheet part)
6L lower nonwoven fabric sheet part (second or first nonwoven fabric sheet part)
7 elastic member
41 convex-concave region
43 non-shaped region
51 concave part
53 convex part
WO waist opening
LO leg opening
T longitudinal direction
L transverse direction
WP waist part
WPE side part (of the waist part)

The invention claimed is:

1. A disposable diaper which is provided with a waist opening and a pair of leg openings, wherein the disposable diaper includes a longitudinal direction and a transverse direction which is perpendicular to the longitudinal direction, a composite stretchable member is provided at least at side parts of a waist part which is positioned between the waist opening and the leg openings of the disposable diaper, the composite stretchable member is provided with a first nonwoven fabric sheet part and a second nonwoven fabric sheet part which are mutually overlaid as well as elastic members which are arranged between the first nonwoven fabric sheet part and the second nonwoven fabric sheet part, each of the first nonwoven fabric sheet part and the second nonwoven fabric sheet part is provided with:

a plurality of convex-concave regions which are provided with convex parts and concave parts which are alternately repeated along the transverse direction and which extend in the longitudinal direction and at least one non-shaped region which separates these convex-concave regions from each other in the longitudinal direction, the first nonwoven fabric sheet part and the second nonwoven fabric sheet part are overlaid so that the convex-concave regions of the first nonwoven fabric sheet part and the second nonwoven fabric sheet part adjoin each other and the non-shaped regions of the first nonwoven fabric sheet part and the second nonwoven fabric sheet part are separated from each other and so that the convex-concave regions and the non-shaped regions are respectively aligned in the longitudinal direction, and the first nonwoven fabric sheet part and the second nonwoven fabric sheet part are joined with each other by an adhesive which is applied to the elastic members.

2. The disposable diaper according to claim 1 wherein the elastic members extend between the non-shaped regions which are separated from each other in the longitudinal direction while being aligned with each other.

3. The disposable diaper according to claim 1 wherein the composite stretchable member extends from one side part to the other side part of the waist part.

4. The disposable diaper according to claim 1 wherein the convex parts of the first nonwoven fabric sheet part enter into the concave parts of the second nonwoven fabric sheet part and wherein the convex parts of the second nonwoven fabric sheet part enter into the concave parts of the first nonwoven fabric sheet part.

5. The disposable diaper according to claim 1 wherein
    the convex parts respectively stick out from the non-shaped regions in terms of the thickness direction, and
    the concave parts respectively reach the non-shaped regions between two adjoining the convex parts.

6. The disposable diaper according to claim 1 wherein the composite stretchable member is formed from a filament nonwoven fabric.

7. The disposable diaper according to claim 1 wherein
    the mutually overlapping first nonwoven fabric sheet part and second nonwoven fabric sheet part are formed in a single nonwoven fabric sheet, and
    the single nonwoven fabric sheet is folded back along a fold line which is parallel to the non-shaped regions and overlaid.

* * * * *